US009062803B2

(12) United States Patent
Bourgeois et al.

(10) Patent No.: US 9,062,803 B2
(45) Date of Patent: Jun. 23, 2015

(54) EXTRUDABLE MULTILAYER TUBING

(71) Applicant: Tekni-Plex, Inc., King of Prussia, PA (US)

(72) Inventors: Philip Bourgeois, Perrysburg, OH (US); Munish Shah, Sylvania, OH (US)

(73) Assignee: Tekni-Plax, Inc., King of Prussia, PA (US)

( * ) Notice: Subject to any disclaimer, the term of this patent is extended or adjusted under 35 U.S.C. 154(b) by 168 days.

(21) Appl. No.: 13/848,889

(22) Filed: Mar. 22, 2013

(65) Prior Publication Data
US 2014/0283940 A1 Sep. 25, 2014

(51) Int. Cl.
*B29C 47/06* (2006.01)
*B29C 47/00* (2006.01)
(Continued)

(52) U.S. Cl.
CPC .............. *F16L 11/04* (2013.01); *B29D 23/001* (2013.01); *B29L 2023/007* (2013.01); *A61M 39/00* (2013.01); *A61M 39/10* (2013.01); *B29C 65/4845* (2013.01); *B29C 65/4895* (2013.01); *B29C 66/1222* (2013.01); *B29C 66/1224* (2013.01); *B29C 47/0004* (2013.01); *B29C 47/0023* (2013.01); *B29C 66/5344* (2013.01); *B29C 66/71* (2013.01); *B29C 66/712* (2013.01); *B29C 47/065* (2013.01); *B29C 66/723* (2013.01); *B32B 25/00* (2013.01); *B32B 27/00* (2013.01); *B29C 69/00* (2013.01); *B29L 2009/00* (2013.01); *B32B 1/08* (2013.01); *F16L 33/01* (2013.01); *B29C 65/1406* (2013.01); *B29C 65/1409* (2013.01); *F16L 9/133* (2013.01)

(58) Field of Classification Search
CPC  B29C 66/00; B29C 66/1122; B29C 66/5221; B29C 66/52272; B29C 66/5344; B29C 66/71; B29C 66/712; B29C 66/723; B29C 65/00; B29C 65/48; B29C 65/4845; B29C 65/4895; B32B 1/08; B32B 25/08; B32B 2597/00; B32B 27/08; B32B 37/00; B32B 37/12; B32B 37/0038; B32B 37/144; B32B 2037/1246; B32B 2037/1253; F16L 11/04; F16L 13/007; F16L 13/103; A61M 39/08
USPC .................. 156/60, 242, 243, 244.11, 244.12, 156/244.13, 244.23, 244.27, 272.2, 275.5, 156/275.7, 293, 294, 296, 303.1, 305, 156/308.2, 308.6; 138/137
See application file for complete search history.

(56) References Cited

U.S. PATENT DOCUMENTS

| 4,578,413 | A | * | 3/1986 | Sterling ......................... 524/269 |
| 2005/0123703 | A1 | * | 6/2005 | Ling et al. .................. 428/36.91 |

(Continued)

OTHER PUBLICATIONS

International Search Report and Written Opinion mailed Aug. 7, 2014 in International Application No. PCT/US2014/031011.

*Primary Examiner* — Philip Tucker
*Assistant Examiner* — Brian R Slawski
(74) *Attorney, Agent, or Firm* — Novak Druce Connolly Bove + Quigg LLP

(57) ABSTRACT

Method of fabricating a polymeric tube for attachment to a prefabricated tubular polymer body comprising: selecting an ethylene copolymer functionalized with a conjugated vinyl moiety, and coextruding an outer tubular layer comprised of the selected functionalized ethylene copolymer together with at least one inner tubular layer comprised of a thermoplastic elastomeric material to form a mating tube having an outer surface comprised of the functionalized ethylene copolymer, a central tubular passage having a longitudinal axis and opposing ends.

11 Claims, 3 Drawing Sheets

(51) Int. Cl.

| | |
|---|---|
| *B29C 65/00* | (2006.01) |
| *B32B 37/00* | (2006.01) |
| *F16L 11/00* | (2006.01) |
| *F16L 11/04* | (2006.01) |
| *A61M 39/00* | (2006.01) |
| *A61M 39/10* | (2006.01) |
| *B29C 65/48* | (2006.01) |
| *B32B 25/00* | (2006.01) |
| *B32B 27/00* | (2006.01) |
| *B29C 69/00* | (2006.01) |
| *B32B 1/08* | (2006.01) |
| *F16L 33/01* | (2006.01) |
| *B29C 65/14* | (2006.01) |
| *F16L 9/133* | (2006.01) |
| *B29D 23/00* | (2006.01) |
| *B29L 23/00* | (2006.01) |
| *B29L 9/00* | (2006.01) |

(56) References Cited

U.S. PATENT DOCUMENTS

| | | |
|---|---|---|
| 2005/0186377 A1 | 8/2005 | Hurst et al. |
| 2006/0178485 A1* | 8/2006 | Shimakage et al. .......... 525/242 |
| 2008/0216827 A1* | 9/2008 | Seydel et al. ............ 128/200.26 |
| 2011/0251596 A1 | 10/2011 | Kim et al. |
| 2012/0064274 A1* | 3/2012 | Cai et al. .................... 428/36.91 |
| 2012/0064356 A1 | 3/2012 | Cai et al. |
| 2012/0150150 A1 | 6/2012 | Cai et al. |

* cited by examiner

EXTRUDABLE MULTILAYER TUBING

FIELD OF THE INVENTION

The present invention relates to the composition, structure and method of making, joining and adhering a polymeric tube together in a co-axial arrangement with another polymeric tubular component where the outer surface of the polymeric tube is inserted within and whose outer surface mates with and is adhered to the inner wall surface of the central passage of the other component.

BACKGROUND

Plasticized PVC tubing has been utilized in the medical field for many decades. Over this time period, there have been many post tube manufacturing operations that have been instituted to add additional fitments at the end of tubes to incorporate the tube into various medical assemblies useful to interact with additional components for the delivery of fluids to a patient useful for human health maintenance or during operational procedures. Typically, these various fitments include a region where a tube is fitted into the fitment assembly and it is then either solvent bonded or adhesively secured to the fitment. Fitments may be made from various materials, including ABS copolymers, polycarbonate and other thermoplastic materials so chosen for their mechanical properties, thermal stability and for the ability to be precisely molded within very tight dimensional tolerances. During the assembly process of combining a tube with a fitment, there is a stage where either a solvent (typically cyclohexanol or cyclohexanone) is applied with an applicator to the external outer surface of the tube and the tube is physically engaged into the fitment. After this step is completed, the solvent eventually evaporates whilst interacting with both the outer surface of the tube and with an inner surface of the fitment. The nature of the solvent is such that it interacts with both surfaces of the tube and fitment and there may be a sort of either physical or chemical bonding means which occurs such that it takes a certain amount of force to physically remove the tube portion from the fitment. This force is typically much larger after the application of solvent to the surfaces versus simply a physical insertion of the tube into the fitment, in the absence of the solvent. In a similar manner, other adhesive technologies utilized comprise UV curable adhesives where instead of a solvent, a liquid adhesive is applied to the surface of the tube and the tube is inserted into the fitment. At the conclusion of fitting the tube to the fitment, this portion of the assembly is exposed to UV (ultraviolet) light which typically activates the adhesive to cure into a final solid form and the tube is adhesively bonded to the fitment. In some instances during assembly, there may exist situations where a fitment is solvent bonded on one end of the tube and at the other end of the tube, a fitment is fitted to the tube with the use of a UV curable adhesive. PVC tubing has been demonstrated to be most useful for all of these operations with a variety of fitments made from the different materials types referenced above. For at least environmental, regulatory and/or legislative reasons, there is a need to avoid the use of plasticized PVC as material with which to make medical tubing.

SUMMARY OF THE INVENTION

The present invention contemplates the manufacture of a multilayered tube preferably comprised of at least two non-PVC containing polymeric materials that are coextruded whereby the two materials are bonded securely to each other and such that the outer tubing layer of the two materials can be readily and securely bonded on an exposed outside surface to the inside surface of the central channel of a conventional tubular component such as a luer or other fitment used in medical treatment applications, particularly luers that are comprised of commercially available polycarbonate or ABS materials commonly used in medical fluid delivery and treatment applications.

In accordance with the invention there is provided a method of coaxially bonding a polymeric tube to a prefabricated tubular body that is comprised of one or more of a polycarbonate, an acrylic or a copolymer containing an acrylonitrile moiety or a copolymer containing an acrylonitrile or acrylic moiety, the prefabricated tubular body defining a hollow central tubular passage having a longitudinal axis bounded by an inner wall, the method comprising:

coextruding an outer tubular layer comprised of an ethylene copolymer functionalized with a conjugated vinyl moiety together with at least one inner tubular layer comprised of a thermoplastic elastomeric material to form a mating tube having an outer surface comprised of the functionalized ethylene copolymer, a central tubular passage having a longitudinal axis and opposing ends, FIG. 3, 300, treating the outer surface of the mating tube along a selected axial length of at least one of the ends with a material that causes the treated outer surface to adhere to the inner wall of the tubular body on curing or drying, FIG. 3, 310, inserting the treated end of the mating tube coaxially into the central tubular passage of the tubular body such that the outer surface of the treated end mates with the inner wall of the tubular body along the selected axial length to form a mated juncture, FIG. 3, 320, and, curing or allowing the mated juncture to dry such that treated outer surface bonds to the inner wall, FIG. 3, 330.

In such a method the step of treating can comprise either coating the outer surface of the at least one end with an alcohol or ketone or a UV or visible light curable containing material.

In such a method the step of curing can comprise at least one of allowing the mated juncture to dry or exposing the mated juncture to UV or visible light for a predetermined amount of time after the treated end of the mating tube is inserted.

In such a method the alcohol or ketone typically comprises an aliphatic alcohol or ketone and the adhesive material comprises an acrylate containing moiety.

Such a method can further comprise selecting the ethylene copolymer to be functionalized with a methyl acrylate containing moiety, an ethyl acrylate containing moiety or a vinyl acetate containing moiety, FIG. 4, 340.

Such a method can further comprise selecting the thermoplastic elastomeric material to be comprised of a polyolefinic elastomeric material.

The outer layer of the mating tube can be comprised of at least about 18% by weight of the conjugated vinyl moiety.

In another aspect of the invention there is provided a bonded tubular assembly comprising:

a prefabricated tubular body comprised of one or more of a polycarbonate, an acrylic or a copolymer containing an acrylonitrile moiety, the prefabricated tubular body defining a hollow central tubular passage having a longitudinal axis bounded by an inner wall, a multilayer mating tube comprised of an outer tubular layer comprised of an ethylene copolymer functionalized with a conjugated vinyl moiety adhered to at least one inner tubular layer comprised of a thermoplastic elastomeric material, the mating tube having an outer surface comprised of the functionalized ethylene copolymer, a central tubular passage having a longitudinal axis and opposing ends, wherein one of the ends of the mating tube is coaxially inserted within the central tubular passage of the prefabricated tubular body such that the outer surface of the one end of the mating tube is mated with the inner wall of the tubular body along a selected axial length of the mating tube, the mated outer surface and inner wall being bonded to each other.

In such an assembly the ethylene copolymer is preferably functionalized with a methyl acrylate containing moiety, an ethyl acrylate containing moiety or a vinyl acetate containing moiety.

In such an assembly the thermoplastic elastomeric material is preferably comprised of a polyolefinic elastomeric material.

In such an assembly the outer layer of the mating tube can be comprised of at least about 18% by weight of the conjugated vinyl moiety.

In another aspect of the invention there is provided a method of fabricating a polymeric tube for attachment to a prefabricated tubular polymer body comprising: selecting an ethylene copolymer functionalized with a conjugated vinyl moiety, FIG. 4, 340, and, coextruding an outer tubular layer comprised of the selected ethylene copolymer together with at least one inner tubular layer comprised of a thermoplastic elastomeric material to form a mating tube having an outer surface comprised of the functionalized ethylene copolymer, a central tubular passage having a longitudinal axis and opposing ends for insertion of at least one end into a central passage of the prefabricated tubular polymer body, FIG. 4, 350.

Such a method can further comprise selecting the functionalized ethylene copolymer to be functionalized with a methyl acrylate containing moiety, an ethyl acrylate containing moiety or a vinyl acetate containing moiety.

Such a method can further comprise selecting the thermoplastic elastomeric material to be comprised of a polyolefinic elastomeric material.

Such a method can further comprise selecting the functionalized ethylene copolymer to be comprised of at least about 18% by weight of the conjugated vinyl moiety.

In another aspect of the invention there is provided a polymeric tube for attachment to a prefabricated tubular polymer body, the polymeric tube comprising:

an outer tubular layer comprised of a selected ethylene copolymer, wherein the outer layer is co-extruded together with at least one inner tubular layer that is comprised of a thermoplastic elastomeric material, the outer and inner co-extruded layers being adhered to each other to form a mating tube having an outer surface comprised of the functionalized ethylene copolymer, a central tubular passage having a longitudinal axis and opposing ends for insertion of at least one end into a central passage of the prefabricated tubular polymer body.

In such a tube the functionalized ethylene copolymer is preferably functionalized with a methyl acrylate containing moiety, an ethyl acrylate containing moiety or a vinyl acetate containing moiety.

In such a tube the thermoplastic elastomeric material preferably comprises a polyolefinic elastomeric material.

In such a tube the functionalized ethylene copolymer can be comprised of at least about 18% by weight of the conjugated vinyl moiety.

BRIEF DESCRIPTION OF THE DRAWINGS

The accompanying drawings illustrate one or more non-limiting examples of the invention.

DETAILED DESCRIPTION OF THE EMBODIMENTS

Reference is made to the exemplary embodiments of the invention with reference to the Figures. Wherever possible, the same reference numbers are used throughout the drawings to refer to the same or like parts.

Figure 1:
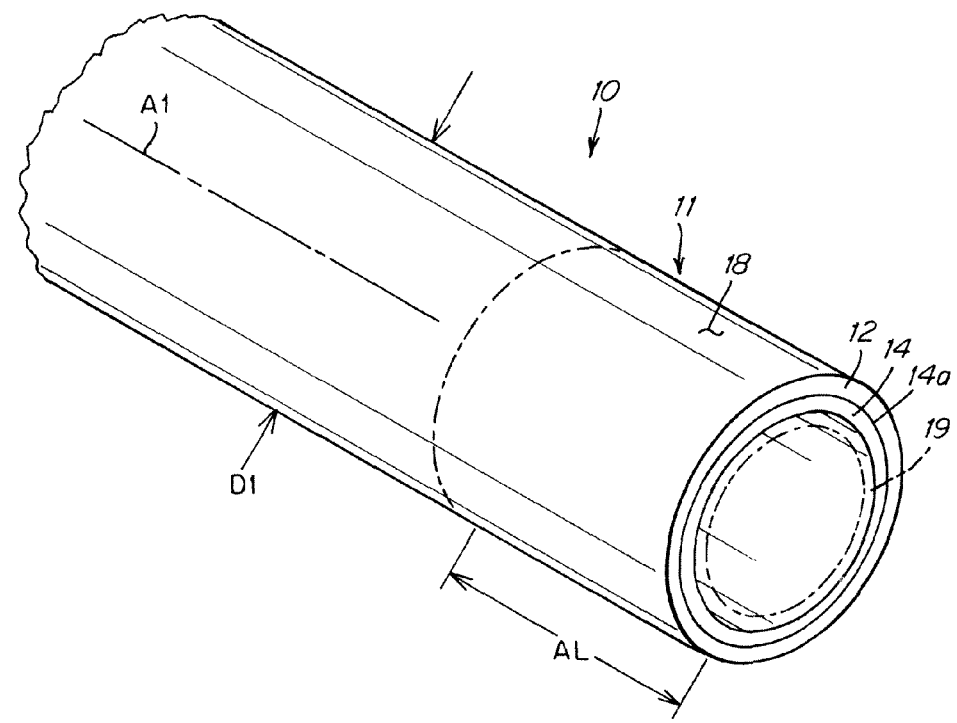
FIG. 1 is a schematic perspective view of a multilayer tube according to the invention having a terminal end portion having a selected axial length AL.
Figure 2:
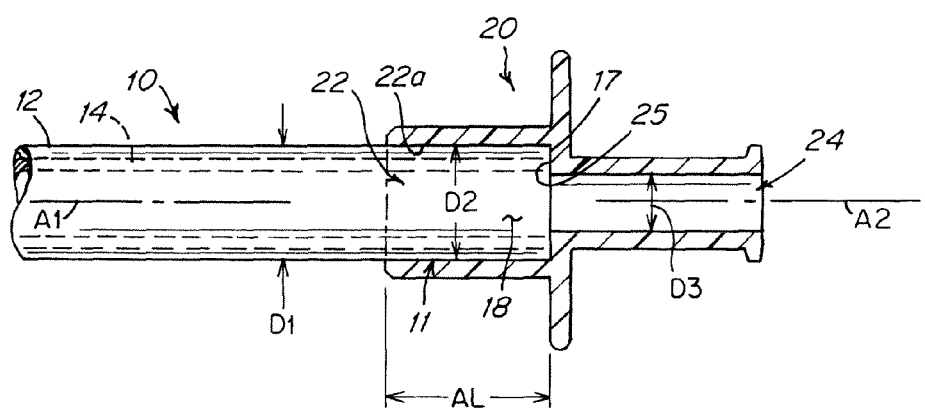
FIG. 2 is a side cross-sectional view of the tube of FIG. 1 with its terminal end portion coaxially inserted within a central fluid flow channel end of a prefabricated tubular body.
Figure 3:
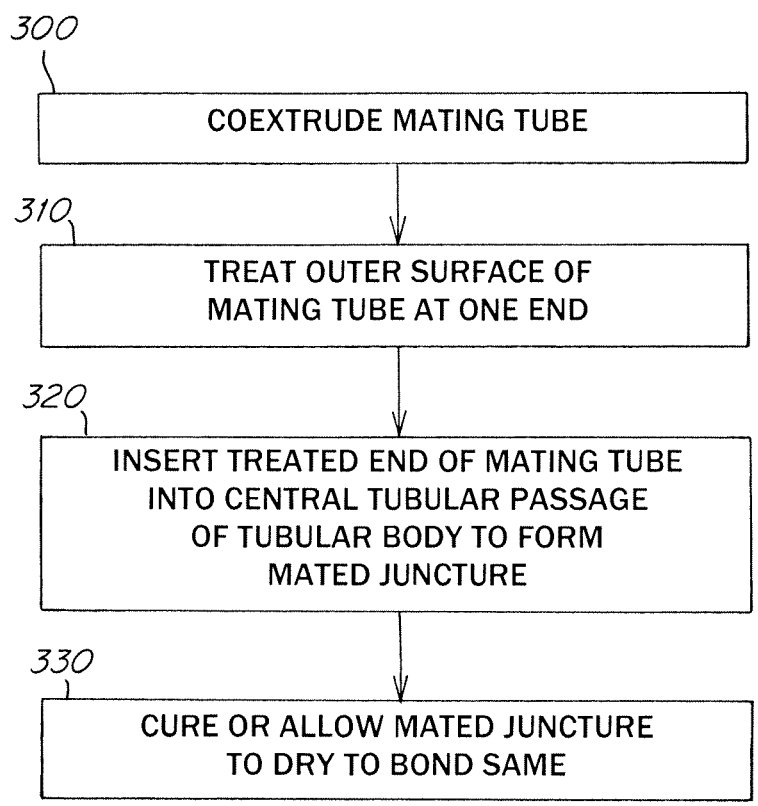
FIG. 3 is a schematic flow chart of one process or method according to the invention.
Figure 4:
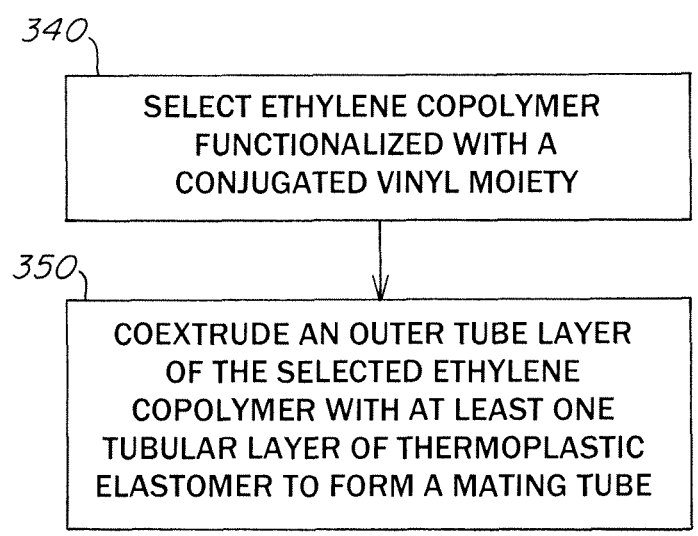
FIG. 4 is a schematic flow chart of another process or method according to the invention.

With reference to FIGS. 1, 2 a mating tube 10 according to the invention is fabricated by co-extruding a first outer layer 12 comprised of a functionalized ethylene copolymer into bonding engagement with the outer surface 14a of a first inner layer 14 comprised of an extrudable thermoplastic elastomeric material. One or more additional layers 19 of extrudable polymeric materials can, as optionally desired, be co-extruded together with the materials of layers 12, 14 into successive bonding engagement with the layers 12, 14 to form a three or more layered tube 10.

The ethylene copolymer layer 12 is typically selected to comprise one or more of an elastomeric or thermoplastic compound that is functionalized with a vinyl moiety that is conjugated within the structure of the polymer such as an acrylate or vinyl acetate moiety. The ethylene copolymer is preferably functionalized with a functional group selected from one or more of methyl acrylate, ethyl acrylate, or vinyl acetate moiety. The functional group typically comprises at least about 18% by weight of the ethylene copolymer.

The ethylene copolymer layer material 12 can include one or more additives as desired including dyes, coloring agents, flame retardants, anti-oxidants, heat resistors, plasticizers, impact resistance modifiers, adhesion promoters, stabilizers and the like.

The thickness of layer 12 typically ranges between about 0.00025" and about 0.010" Examples of commercially available ethylene copolymers are Westlake EMAC® SP2268, an ethylene-methyl-acrylate copolymer which has 24 wt % methyl acrylate comonomer, Westlake Tymax GA7001, an anhydride modified ethylene methyl acrylate copolymer available from Westlake Chemical, Westlake Center, 2801 Post Oak Boulevard, Houston, Tex., Dow EA 103, an ethylene-ethyl acrylate copolymer which has 19.5 wt % ethyl acrylate comonomer and, DuPont Elvax 260, an ethylene-vinyl acetate copolymer which has 28 wt % vinyl acetate comonomer, and Celanese Ateva 1821A, an ethylene-vinyl acetate copolymer which has 18 wt % vinyl acetate comonomer.

The thermoplastic elastomeric material (TPE) of which the first inner layer 14 is comprised is preferably a polyolefinic elastomeric material and is preferably one or more polymers that are extrudable, are processable as a melt at elevated temperature, do not have significant creep, are of generally low modulus and are flexible materials that can be stretched repeatedly at room temperature with an ability to return to their approximate original length when stress is released. Of the generally recognized types of TPEs, the following traditional types, namely two-phase systems comprised of a hard thermoplastic phase coupled mechanically or chemically with a soft elastomer phase which results in a TPE that has the combined properties of the two phases, and the newer types of TPEs, namely metallocene-catalyzed polyolefin plastomers & elastomers, and reactor-made thermoplastic polyolefin elastomers, are suitable for use in layer 14. Amongst the traditional TPEs are: a) styrenic diblock and triblock copolymers which include a hard polystyrene phase and an elastomeric polyolefinic phase based on ethylene, butadiene, isoprene or hydrogenated butadiene, b) polyolefin based blends that include ethylenic and propylenic rubbers compounded into a polyethylene or polypropylene material and c) polyolefin based alloys that include a vulcanized rubber component compounded into a polyethylene or polypropylene material. Amongst the new types of TPEs are: a) metallocene catalyzed polyethylene copolymers which include various linear short chain alpha olefin alkenes as a comonomer, such as butadiene, hexene or octene, b) dual reactor based polyolefins wherein a hard phase such as polypropylene is made in one reactor and is transferred to another reactor wherein an elastomeric material such as polyethylene-propylene rubber is polymerized in situ within the hard phase, c) polyolefin elastomers which comprise various polyethylene block copolymers based on a polyethylene block and a polyethylene-octene block and d) very low molecular weight linear low density polyethylenes.

Exxon 4049 is one example of a suitable commercially available TPE and any of the aforementioned TPEs may be utilized in layer 14.

The TPE material of layer 14 can include one or more additives as desired including dyes, coloring agents, flame retardants, anti-oxidants, heat resistors, plasticizers, impact resistance modifiers, adhesion promoters, stabilizers and the like.

The tubular body 20 is typically formed into the configuration of a luer, plastic tube connector or other fitment that is used in medical applications such as for connecting tubes for delivery of medical fluids from a fluid source to a patient or receptacle in a sterile manner where the fluid is sealed within a closed system, the tubing and connector maintaining the fluid contained within the sealed system. The tubular body 20 is most preferably comprised of a stable prefabricated polymeric material. The polymeric material of which tubular body 20 is comprised is typically a polycarbonate or ABS (acrylonitrile-butadiene-styrene copolymer) material but can also be an acrylic resin, polyester, polyacetal or polyamide such as nylon.

The polymeric material of which tubular body 20 is comprised can include one or more additives as desired including dyes, coloring agents, flame retardants, anti-oxidants, heat resistors, impact resistance modifiers, stabilizers and the like.

The tube 10 has a terminal end 11 having an outer surface 18 and a selected axial length AL for purposes of insertion into passage 22 and bonding to the inner wall surface 22a of the central fluid passage 22 of tubular body 20 (typically in the form of a luer). As shown in FIGS. 1, 2, the end 11 of the tube is inserted into passage 22 of body 20 such that axis A1 is generally coaxially aligned with the axis A2 of the tubular body 20. The cross-sectional diameter D2 of the passage 22 is preferably complementary to the cross-sectional diameter D1 of the end 11 of the tube 10. The diameter D2 can be slightly smaller than D1 (0.01 to about 0.5 microns smaller) in order to ensure a snug fit of the end 11 within passage 22. On insertion of end 11 into passage 22, the outer surface 18 engages against the inner surface 22a of passage 22 and the solvent or adhesive that has been applied to surface 18 prior to insertion is securely spread over both surfaces 18 and 22a along the entire selected axial length AL.

The tubular body 20 typically has separate co-axially aligned A1-A2 hollow central passage portions 22, 24 that have different cross-sectional diameters D2 and D3 where D3 is typically larger than D2 thus forming a stop surface 25 against which the wider D1 terminal end surface 17 of the terminal end 11 of tube 10 (about the same or slightly larger than D2) is stopped and abuts against on forcible manual insertion of end 11 axially into and through passage 22.

Where solvent is the choice of surface 18 treatment, the solvent is typically selected from one or more of cyclohexanol, cyclohexanone, toluene, xylenes, tetrahydrofuran, 2-methyltetrahydrofuan and methyl ethyl ketone. Solvent treatment typically comprises applying solvent to surface 18 of the end 11 of tube 10 prior to inserting the end 11 into the axial passage 22 of the tubular body 20. Where adhesive is the choice of surface 18 treatment, the adhesive is most preferably a UV or visible curable liquid. The adhesive preferably comprises an acrylate compound such as a cyanoacrylate, epoxy, silicone or polyurethane.

Test Results:

A variety of tubing specimens were fabricated by extrusion in monolayer and by co-extrusion multilayer forms using materials as specified in Table I below using extrusion tooling such as the "Tri Die" extrusion apparatus manufactured by the Genca Division of General Cable Company, Clearwater, Fla. The tubing specimens were extruded with dimensions of: 0.187" OD×0.125" ID and overall wall thickness=0.0315" with an outer skin layer for bonding of 5.5 mil+/−1.5 mil. As known in the art, the extrusion or co-extrusion process is carried out by melting the polymeric material(s), routing the melted material(s) under pressure through a suitable die head to form a tubular shaped extrudate or co-extrudate that is then cooled through conventional water baths or water vacuum tanks to form an end product. Tubing specimens so fabricated were then bonded to commercially available luers as specified below and then pull tested for bond strength. The test samples were prepared and test equipment and parameters utilized were as follows:

Samples Prepared Using UV Cured Adhesive:
1. Tube Samples were cut to 8 inches and an end of tube cleaned with 70% isopropyl alcohol and allowed to air dry.
2. UV adhesive applied to ½ inch length of the cleaned end of tube with small applicator and inserted into luer. The UV adhesive used: MD Medical Device, UV Light Curing Adhesive and Coatings, Ultra Light-Weld®1191-M, Dymax Corporation, Adhesives & Adhesive Equipment, 318 Industrial Lane, Torrington, Conn. 06790
3. Tubes were then cured for 45 seconds using a UV lamp: Loctite, Zeta 7411, Model 98027, UV Flood Curing System, Rocky Hill, Conn. 06067, SN0603A23
4. Tubes were tested 24 hours afterward (72F/50% RH)

Samples Prepared Using Solvent (Cyclohexanone) Bonding:
1. Tubes samples were cut to 8 inches and the end of the tube was cleaned with 70% isopropyl alcohol and allow to air dry.
2. Cyclohexanone (100% neat) was applied to % inch of the cleaned end of tube with small applicator and inserted into the luer.
3. Tubes were set to dry for 24 hours prior to mechanical testing (72F/50% RH)

Mechanical Test Equipment and Parameters used in Testing of tubing assemblies that were bonded to commercially available ABS and polycarbonate luers as specified below.

Mechanical test equipment which can test samples in a tensile manner and record forces on the sample are well known in the art and such equipment such as those manufactured by Instron (826 University Avenue, Norwood, Mass., USA) or Lloyd Instruments Ltd (West Sussex, UK) are useful for testing. Such instruments include load cells attached to a moveable clamp and include an immovable clamp or jaw. Usually, a sample is clamped between the top and bottom clamps and one clamp is moved at a control rate and records the force which a sample is experiencing whilst the clamp is moving. In the test described below, the tube and luer assembly is secured within the equipment clamps and the maximum force, in pounds, to remove the tube from the luer is measured. Such a test is referred to as a pull test:

1. Test equipment clamps are set 3 inches apart
2. Luer end of tube clamped in center of the upper clamp
3. Loose end of tube clamped in center of the lower clamp.
4. The pull test initiated and allowed to cycle through until the tube is pulled from luer at a rate of 5 inches per minute.
5. The pound force (lbs) to pull tube from luer is recorded and the tube is removed from the clamps.
6. Repeated steps 1-5 for each sample (10×) for each type of luer/tube combination.

Commercially Available Luer Specimens Used in Assembly and Pull Tests were Purchased from Qosin.com with the Following Identification and Specifications:

1. Part Number 11150, Female Luer Lock Connector, 0.192 inch-0.183 inch ID/0.254 inch-0.260 inch OD, Material: Polycarbonate
2. Part Number 65252, Female Luer Connector, Clear, 0.197 inch-0.185 inch ID, Material: ABS.

The specimen tubes that were fabricated for pull testing purposes were fabricated in both monolayer and multilayer format, designated in the following Table I as M or MLX respectively. The specimen tubes that were tested were fabricated from commercially available TPE and functionalized ethylene copolymer materials which are specified below immediately following Table I. In each case where a multilayer (MLX) specimen was fabricated, the outer layer of the MLX specimen was comprised of the functionalized ethylene copolymer.

TABLE I

| Sample Tube Material | Monolayer (M)- Multilayer (MLX) | Solvent | ABS Luer Pull Force (lbs) | STD DEV | PC Luer Pull Force (lbs) | STD DEV |
|---|---|---|---|---|---|---|
| [1] TPE | M | CycloHexanone | 1.28 | 0.57 | 3.60 | 0.81 |
| (2) 70 TPE/ 30 MAH Conc | M | CycloHexanone | 1.39 | 0.51 | 3.43 | 0.53 |
| [3] 50 TPE/ 50 MAH Conc | M | CycloHexanone | 1.32 | 0.40 | 3.40 | 0.83 |
| [4] MAH | M | CycloHexanone | 2.15 | 0.92 | 4.48 | 1.45 |
| [5] EEA | M | CycloHexanone | 5.45 | 1.19 | 8.37 | 0.71 |
| [6] 28 wt % EVA | M | CycloHexanone | 5.45 | 1.25 | 6.96 | 0.84 |
| [7] EMA | M | CycloHexanone | 3.00 | 1.07 | 6.96 | 0.65 |
| [8] EMA-MAH copolymer | M | CycloHexanone | 3.02 | 0.35 | 5.76 | 0.57 |
| [9] EEA/TPE | MLX | CycloHexanone | 3.12 | 0.70 | 5.96 | 0.49 |
| [10] 28 wt % EVA/ TPE | MLX | CycloHexanone | 4.66 | 0.77 | 5.46 | 0.55 |
| [11] 18 wt % EVA/ TPE | MLX | CycloHexanone | 3.06 | 1.50 | 5.65 | 0.74 |

| Material | Construction Monolayer (M)- Multilayer (MLX) | Adhesive | ABS Luer Pull Force (lbs) | STD DEV | PC Luer Pull Force (lbs) | STD DEV |
|---|---|---|---|---|---|---|
| [12] TPE | M | UV | 4.20 | 1.31 | 4.89 | 0.51 |
| (13) 70 TPE/ 30 MAH Conc | M | UV | 4.32 | 0.48 | 5.17 | 0.36 |
| [14] 50 TPE/ 50 MAH Conc | M | UV | 3.80 | 0.53 | 4.55 | 0.31 |
| [15] EEA/TPE | MLX | UV | 5.58 | 0.85 | 6.03 | 0.41 |
| [16] 28 wt % EVA/ TPE | MLX | UV | 4.64 | 0.55 | 6.53 | 0.87 |
| [17] 18 wt % EVA/ TPE | MLX | UV | 4.57 | 1.01 | 5.38 | 0.55 |

Table I, Sample Tubes—Materials Extruded or Coextruded Monolayer—Solvent Bonded to Luer
[1] 100% Exxon EXACT 4049
[2] (Blend) 70 wt % Exxon EXACT 4049/30 wt % Dow Amplify 1052H
[3] (Blend) 50 wt % Exxon EXACT 4049/50 wt % Dow Amplify 1052H
[4] 100% Dow Amplify 1052H, a highly concentrated maleic anhydride modified polyolefin available from Dow.
[5] 100% Dow EA 103
[6] 100% DuPont Elvax 260
[7] 100% Westlake 2268
[8] 100% Westlake GA 7001 (EMA/Maleic Anhydride copolymer)
BiLayer—Outer layer Solvent Bonded to Luer
[9] Outer—100% Dow EA 103/Inner—100% Exxon EXACT 4049
[10] Outer—100% DuPont Elvax 260/Inner—100% Exxon EXACT 4049

[11] Outer—100% Celanese Ateva EVA 1821A/Inner—100% Exxon 4049

Monolayer—Adhesive Bonded To Luer

[12] 100% Exxon EXACT 4049

[13] (Blend) 70 wt % Exxon EXACT 4049/30 wt % Dow Amplify 1052H

[14] (Blend) 50 wt % Exxon EXACT 4049/50 wt % Dow Amplify 1052H

BiLayer—Outer Layer Adhesive Bonded to Luer

[15] Outer—100% Dow EA 103/Inner—100% Exxon EXACT 4049

[16] Outer—100% DuPont Elvax 260/Inner—100% Exxon EXACT 4049

[17] Outer—100% Celanese EVA 1821A/Inner—100% Exxon EXACT 4049

As shown by the Table I data, a multi-layered tube 10 having an outer surface layer (whether in multilayer or monolayer form) that is comprised of the least effective functionalized polymer composition (18 wt % EVA/TPE) provides a significant improvement in bonding strength relative to a typical non-polar polymeric material (TPE). As shown by the data, the bonding strength of the least effective functionalized polymeric material (18 wt % EVA/TPE) was at least about 3 lbs using solvent and at least about 4.5 lbs using UV curable adhesive (bonded to an ABS luer) as compared with a bonding strength of a non-functionalized polymer (TPE) of less than about 1.3 lbs (solvent method) and less than about 4.2 lbs (UV curable adhesive) when bonded to an ABS luer.

Also as shown by the data, the bonding strength for one of the least effective functionalized polymeric materials (18 wt % EVA/TPE) when bonding to a polycarbonate luer was at least about 5.46 lbs using solvent and at least about 5.38 lbs using adhesive as compared with a bonding strength for a non-functionalized polymer (TPE) of about 3.60 lbs using solvent and about 4.89 lbs using adhesive.

What is claimed is:

1. A method of coaxially bonding a polymeric tube to a prefabricated tubular body defining a hollow central tubular passage having a longitudinal axis bounded by an inner wall that is comprised of one or more of a polycarbonate, an acrylic or a copolymer containing an acrylonitrile, the method comprising:

coextruding an outer tubular layer comprised of an ethylene copolymer functionalized with a conjugated vinyl moiety together with at least one inner tubular layer comprised of a thermoplastic elastomeric material to form a mating tube having an outer surface comprised of the functionalized ethylene copolymer, a central tubular passage having a longitudinal axis and opposing ends, treating the outer surface of the mating tube along a selected axial length of at least one of the ends with an alcohol or ketone or a UV or visible light curable containing material that causes the treated outer surface to adhere to the inner wall of the tubular body on curing or drying, inserting the treated end of the mating tube coaxially into the central tubular passage of the tubular body such that the outer surface of the treated end mates with the inner wall of the tubular body along the selected axial length to form a mated juncture, curing or allowing the mated juncture to dry such that the treated outer surface bonds to the inner wall.

2. The method of claim 1 wherein the step of treating comprises coating the outer surface of the at least one end with the UV or visible light curable containing material.

3. The method of claim 2 wherein the step of curing comprises exposing the mated juncture to UV or visible light for a predetermined amount of time after the treated end of the mating tube is inserted.

4. The method of claim 1 wherein the alcohol or ketone comprises an aliphatic alcohol or ketone and the adhesive material comprises an acrylate containing moiety.

5. The method of claim 1 further comprising selecting the ethylene copolymer to be functionalized with a methyl acrylate containing moiety, an ethyl acrylate containing moiety or a vinyl acetate containing moiety.

6. The method of claim 1 further comprising selecting the thermoplastic elastomeric material to be comprised of a polyolefinic elastomeric material.

7. The method of claim 1 wherein the outer layer of the mating tube is comprised of at least about 18% by weight of the conjugated vinyl moiety.

8. Method of fabricating a polymeric tube for attachment to a prefabricated tubular polymer body having an inner wall that is comprised of one or more of a polycarbonate, an acrylic or a copolymer containing an acrylonitrile comprising:

selecting an ethylene copolymer functionalized with a conjugated vinyl moiety, coextruding an outer tubular layer comprised of the selected ethylene copolymer together with at least one inner tubular layer comprised of a thermoplastic elastomeric material to form a mating tube having an outer surface comprised of the functionalized ethylene copolymer, a central tubular passage having a longitudinal axis and opposing ends for insertion of at least one end into a central passage of the prefabricated tubular polymer body, treating one end of the outer surface of the outer tubular layer with an alcohol or ketone or a UV or visible light curable containing material that causes the treated outer surface to adhere to the inner wall of the tubular body on insertion of the one end of the outer tubular layer into the tubular body along a selected axial length of the tubular body, and curing or drying the material treated on the outer surface when mated with the inner surface of the prefabricated tubular body.

9. The method of claim 8 further comprising selecting the functionalized ethylene copolymer to be functionalized with a methyl acrylate containing moiety, an ethyl acrylate containing moiety or a vinyl acetate containing moiety.

10. The method of claim 8 further comprising selecting the thermoplastic elastomeric material to be comprised of a polyolefinic elastomeric material.

11. The method of claim 8 further comprising selecting the functionalized ethylene copolymer to be comprised of at least about 18% by weight of the conjugated vinyl moiety.

* * * * *